US011330981B2

(12) United States Patent
Andersen et al.

(10) Patent No.: US 11,330,981 B2
(45) Date of Patent: May 17, 2022

(54) METHOD AND APPARATUS FOR A BURST OPERATION PRESSURE SENSOR

(71) Applicant: Pacesetter, Inc., Santa Clara, CA (US)

(72) Inventors: Dean Andersen, San Jose, CA (US); William Douglas Barrett, Tucker, GA (US); Jin-Woo Park, Duluth, GA (US); Philip M. Fitzsimons, Lilburn, GA (US); Ion Opris, San Jose, CA (US); Eiji Shirai, Mountain View, CA (US)

(73) Assignee: Pacesetter, Inc., Sylmar, CA (US)

( * ) Notice: Subject to any disclaimer, the term of this patent is extended or adjusted under 35 U.S.C. 154(b) by 694 days.

(21) Appl. No.: 16/226,921

(22) Filed: Dec. 20, 2018

(65) Prior Publication Data

US 2020/0196867 A1 Jun. 25, 2020

(51) Int. Cl.
| | |
|---|---|
| *A61B 5/1455* | (2006.01) |
| *A61B 5/00* | (2006.01) |
| *A61B 5/07* | (2006.01) |
| *A61B 5/05* | (2021.01) |
| *A61B 5/0215* | (2006.01) |

(52) U.S. Cl.
CPC ............ *A61B 5/0031* (2013.01); *A61B 5/076* (2013.01); *A61B 5/686* (2013.01); *A61B 5/0215* (2013.01); *A61B 5/05* (2013.01); *A61B 2560/0219* (2013.01); *A61B 2560/0223* (2013.01)

(58) Field of Classification Search
None
See application file for complete search history.

(56) References Cited

U.S. PATENT DOCUMENTS

| | | | |
|---|---|---|---|
| 7,245,117 B1 | 7/2007 | Joy et al. | |
| 7,498,799 B2 | 3/2009 | Allen et al. | |
| 7,909,770 B2 | 3/2011 | Stern et al. | |
| 8,264,240 B2 | 9/2012 | Park et al. | |
| 9,792,469 B1 | 10/2017 | Park | |
| 10,098,551 B2 | 10/2018 | Doan et al. | |
| 2006/0287700 A1 | 12/2006 | White et al. | |
| 2013/0165801 A1 | 6/2013 | Min | |
| 2013/0178751 A1 | 7/2013 | Min | |
| 2014/0018644 A1 | 1/2014 | Colvin et al. | |
| 2014/0100627 A1 | 4/2014 | Min | |
| 2014/0213915 A1 | 7/2014 | Doan et al. | |

*Primary Examiner* — Marjan Fardanesh
(74) *Attorney, Agent, or Firm* — Vierra Magen Marcus LLP

(57) ABSTRACT

Embodiments described herein relate to an implantable device that include an inductor coil, a storage capacitor, active circuitry, and a sensor, but doesn't include an electrochemical cell, and methods for use therewith. During first periods of time, the storage capacitor accumulates and stores energy received via the inductor coil from a non-implanted device. During second periods of time, interleaved with the first periods of time, and during which energy is not received from the non-implanted device, the active circuitry of the implantable device is powered by the energy stored on the storage capacitor and is used to perform at least one of a plurality of predetermined operations of the implantable device, including, e.g., obtaining a sensor measurement from the sensor of the implantable device, transmitting a communication signal including a sensor measurement to the non-implanted device, and/or receiving a communication signal from the non-implanted device.

21 Claims, 5 Drawing Sheets

METHOD AND APPARATUS FOR A BURST OPERATION PRESSURE SENSOR

FIELD OF TECHNOLOGY

Embodiments of the present technology generally relate to implantable devices that includes at least one physiologic sensor and that enable sensor measurements to be interrogated wirelessly.

BACKGROUND

There exist various different types of implantable devices that include at least one physiologic sensor and that enable measurements of physiologic properties, sensed using the sensor(s), to be interrogated wirelessly. Most such implantable devices include a battery having one or more electrochemical cells and that may or may not be rechargeable. A problem with implantable devices that include a non-rechargeable battery is that they are rendered inoperable once the battery is dead. A problem with implantable devices that include a rechargeable battery is that they cannot be used when the battery is dead, and they eventually get to the point that they can no longer be charged due to changes over time in the one or more electrochemical cells of the rechargeable battery.

There exists a commercially available implantable pressure sensor device that is devoid of an electrochemical cell yet still allows pressure measurements to be interrogated wirelessly using a non-implanted device. This implantable device is part of the CardioMEMS™ System that is available from St. Jude Medical (headquartered in St. Paul, Minn.), which is a subsidiary of Abbott Laboratories (headquartered in Abbott Park, Ill.). Such a device, which can be implanted in a patient in order to monitor pulmonary artery pressure (PAP) of the patient, operates based on an LC resonant principle. More specifically, such an implantable device includes a pressure sensing capacitor, whose capacitance changes with changes in pressure (and is thus indicative of pressure), and an inductor in parallel with the capacitor, to form an LC circuit, which can also be called a resonant circuit, tank circuit, or tuned circuit. As the capacitance indicative of pressure changes, the resonant frequency of the LC circuit changes, and thus the resonant frequency of the sensor is a function of the sensed pressure. Accordingly, as the sensed pressure changes, the resonant frequency also changes. To determine the resonant frequency of the sensor of the implantable device, a non-implanted device (which can also be referred to as an external interrogator device, or an external device) monitors the implantable device to determine its resonant frequency and thereby determines the pressure measured or sensed by the sensor. The non-implanted device that is used to interrogate such an implantable device requires a relatively sophisticated electronics architecture, which may be relatively expensive. Further, this implantable device includes only electrically passive components that are capable of providing very limited amounts of information (i.e., only measures indicative of pressure) to the non-implanted device.

SUMMARY

Certain embodiments of the present technology relate to an implantable device that includes an inductor coil, a storage capacitor, active circuitry, and a sensor, but does not include an electrochemical cell for powering the active circuitry. Certain embodiments of the present technology relate to methods for use with such an implantable device. Such a method includes during first periods of time, using the storage capacitor to accumulate and store energy received via the inductor coil from a non-implanted device. The method also includes during second periods of time that are interleaved with the first periods of time, and during which energy is not received from the non-implanted device, using the active circuitry of the implantable device, which is powered by the energy stored on the storage capacitor, to perform at least one of a plurality of predetermined operations of the implantable device. In accordance with an embodiment, the plurality of predetermined operations includes obtaining a sensor measurement from the sensor of the implantable device, transmitting a communication signal including a sensor measurement to the non-implanted device, and receiving a communication signal from the non-implanted device. During at least some of the second periods of time, the active circuitry of the implantable device is used to obtain sensor measurements from the sensor of the implantable device.

In accordance with certain embodiments, during the first periods of time the inductor coil of the implantable device receives AC power signals from the non-implanted device, and the implantable device converts the AC power signals to DC signals that are used to charge the storage capacitor of the implantable device. During the second periods of time (that are interleaved with the first periods of time) the inductor coil of the implantable device does not receive AC power signals from the non-implanted device, and thus, communications signals transmitted between the implantable device and the non-implanted device are subject to less noise compared to if the communications signals were transmitted at the same times that the inductor coil of the implantable device receives AC power signals from the non-implanted device. Additionally, during the second periods of time one or more sensor measurements that are obtained by one or more sensors of the implantable device are subject to less noise compared to if the sensor measurements are transmitted at the same times that the inductor coil of the implantable device receives AC power signals from the non-implanted device. The first periods of time can also be referred to a burst periods or energy harvest periods. The second periods of time can also be referred to as quiet periods or energy quiet periods.

In accordance with certain embodiments, the implantable device also includes memory that can store one or more sensor measurements therein prior to the sensor measurement(s) being transmitted to the non-implanted device. The memory can additionally or alternatively store program code for operating the implantable device, a patient identifier, an identifier of the implantable device, and/or calibration data for the implantable device. Such calibration data can include, e.g., non-linearity calibration data and offset calibration data, but is not limited thereto.

In accordance with certain embodiments, the same inductor coil of the implantable device, which is used to receive energy from the non-implanted device during the first periods of time, is also used for transmitting and receiving communications signals to and from the non-implanted device during at least some instances of the second periods of time.

In accordance with certain embodiments, the sensor of the implantable device is a passive capacitive pressure sensor whose capacitance changes with changes in pressure and is thereby indicative of pressure. In such embodiments, the method can also include using the active circuitry to obtain sensor measurements from the passive capacitive pressure sensor and to convert the sensor measurements from analog measurements to digital measurements that are stored in the memory and/or transmitted in one or more communication signals from the implantable device to the non-implanted device.

In accordance with certain embodiments, the implantable device includes one or more reference capacitors, and the active circuitry is used from time-to-time to obtain reference capacitance measurements of at least one of the one or more reference capacitors and convert the reference capacitance measurements from analog measurements to digital measurements that are stored in memory and/or transmitted in one or more communication signals from the implantable device to the non-implanted device. Changes over time in the reference capacitance measurements are indicative of drift in the active circuitry. Accordingly, the reference capacitance measurements can be used by the implantable device, or the non-implanted device, to compensate for the drift in the active circuitry.

In accordance with certain embodiments, the implantable device is configured to be implanted in a pulmonary artery, and the sensor measurements obtained using the sensor of the implantable device are indicative of pulmonary artery pressure (PAP).

In accordance with certain embodiments, the implantable device can detect a transition from an instance of the first period of time (aka the burst period or energy harvest period) to an instance of the second period of time (aka the quiet period or energy quiet period), and in response thereto, triggers use of the active circuitry configured to obtain sensor measurements from the passive capacitive pressure sensor and convert the sensor measurements from analog measurements to digital measurements. The implantable device can also detect a transition from an instance of the second period of time (aka the quiet period or energy quiet period) to an instance of the first period of time (aka the burst period or energy harvest period), and in response thereto, stop sending communication signals and/or stop obtaining sensor measurements.

In accordance with certain embodiments, the memory of the implantable device includes non-volatile memory, and the method further includes storing device specific information in the non-volatile memory. The device specific information can include a patient identifier indicative of a patient in which the implantable device is implanted, sensor linearity calibration data that is used to compensate for a non-linearity of the sensor, and sensor offset calibration data that is used to compensate for an offset in sensor measurements. Other variations are also possible. In accordance with certain embodiments, during one or more instances of the second periods of time, the operation performed by the active circuitry comprises transmitting one or more communication signals including the device specific information from the implantable device to the non-implanted device.

In accordance with certain embodiments of the present technology, an implantable device includes a hermetic housing and an inductor coil, a storage capacitor, active circuitry, a sensor, and memory all within the hermetic housing. The active circuitry includes at least a controller (e.g., an MCU) and a communication interface. The controller is configured to control other portions of the active circuitry including the communication interface. The communication interface is configured to enable wireless communication between the implantable device and a non-implanted device. The implantable device is devoid of an electrochemical cell for powering the active circuitry. The storage capacitor is configured to accumulate and store energy received via the inductor coil of the implantable device from a non-implanted device during first periods of time. The active circuitry of the implantable device, which is powered by the energy stored on the storage capacitor, is configured to perform at least one of a plurality of predetermined operations of the implantable device during second periods of time that are interleaved with the first periods of time. During one or more instances of the second periods of time, the operation performed by the active circuitry includes obtaining a sensor measurement from the sensor of the implantable device and storing the sensor measurement in the memory of the implantable device. During one or more further instances of the second periods of time, the operation performed by the active circuitry includes transmitting one or more communication signals including one or more of the sensor measurements from the implantable device to the non-implanted device. During one or more additional instances of the second periods of time, the operation performed by the active circuitry includes receiving one or more communication signals from the non-implanted device.

In accordance with certain embodiments, the same inductor coil of the implantable device, which is used to receive energy from the non-implanted device during the first periods of time, is also used for the transmitting and the receiving of the communications signals to and from the non-implanted device during at least some of the instances of the second periods of time.

In accordance with certain embodiments, the implantable device also includes a rectifier coupled between the inductor coil and the storage capacitor. The rectifier is configured to convert AC power signals, received from the non-implanted device, to DC signals that are used to charge the storage capacitor of the implantable device during the first periods of time that the inductor coil receives the AC power signals from the non-implanted device. During the second periods of time the inductor coil of the implantable device does not receive AC power signals from the non-implanted device, and thus, communications signals transmitted between the implantable device and the non-implanted device using the inductor coil of the implantable device are subject to less noise compared to if the communications signals were transmitted at the same times that the inductor coil of the implantable device receives AC power signals from the non-implanted device.

In accordance with certain embodiments, the sensor is a passive capacitive pressure sensor whose capacitance changes with changes in pressure and is thereby indicative of pressure. Additionally, the active circuitry can include sensor measurement circuitry that is configured to obtain sensor measurements from the passive capacitive pressure sensor and convert the sensor measurements from analog measurements to digital measurements, which can be transmitted in one or more communication signals from the implantable device to the non-implanted device.

In accordance with certain embodiments, the implantable device is configured to be implanted in a pulmonary artery, and the sensor measurements obtained using the passive capacitive pressure sensor are indicative of pulmonary artery pressure (PAP).

In accordance with certain embodiments, the active circuitry includes circuitry configured to detect a transition from an instance of the first period of time to an immediately following instance of the second period of time, and in response thereto, trigger use of the sensor measurement circuitry. Such circuitry can also detect a transition from an instance of the second period of time to an immediately following instance of the first period of time, and in response thereto, trigger use of the communication interface and/or stop the use of the sensor measurement circuitry.

In accordance with certain embodiments of the present technology, during one or more instances of the second periods of time, the operation performed by the active circuitry comprises transmitting one or more communication signals including device specific information from the implantable device to the non-implanted device.

This summary is not intended to be a complete description of the embodiments of the present technology. Other features and advantages of the embodiments of the present technology will appear from the following description in which the preferred embodiments have been set forth in detail, in conjunction with the accompanying drawings and claims.

DETAILED DESCRIPTION

Figure 1:
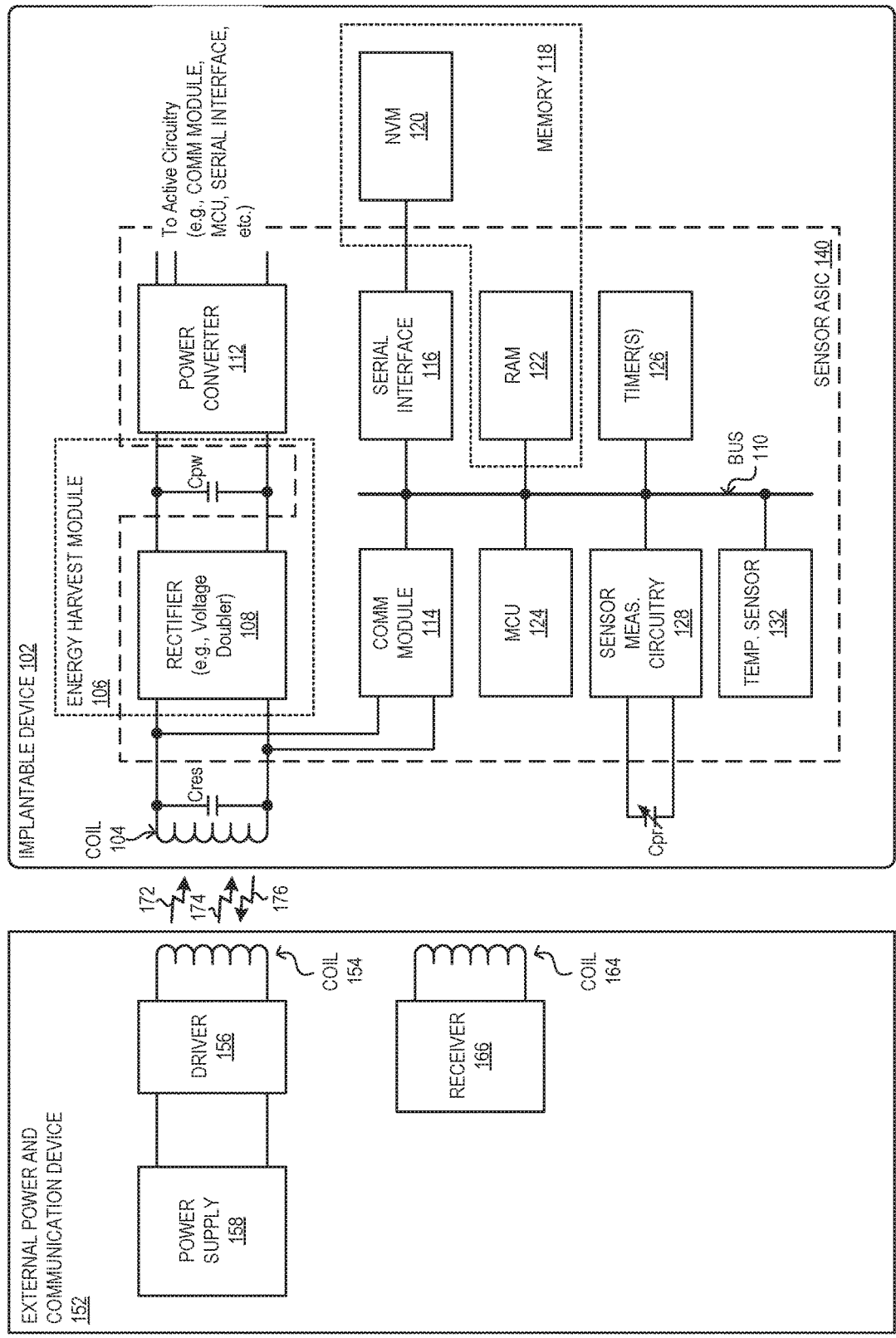
FIG. 1 illustrates an implantable device, according to an embodiment of the present technology, and an external device (aka a non-implanted device) that is capable of powering and communicating with the implantable device.

FIG. 1 illustrates an implantable device 102, according to an embodiment of the present technology, and an external device 152 that is capable of powering and communicating with the implantable device 102. The implantable device 102, once implanted in a patient, can also be referred to as an implanted device 102. The external device 152 can also be referred to as a non-implanted device 152, an interrogation device 152, or the like.

Referring to FIG. 1, the implantable device 102 is shown as including an inductor coil 104, a rectifier 108, an energy storage capacitor Cpw, and a power converter 112. The implantable device 102 is also shown as including a communication module 114, a serial interface 116, random access memory (RAM) 122, one or more timers 126, a microcontroller unit (MCU) 124, sensor measurement circuitry 128, and a temperature sensor 132, each of which is shown as being connected to a bus 110. The serial interface 116 is connected between non-volatile memory (NVM) 120 and the bus 110. The implantable device 102 also includes a capacitor Cpr that is capable of sensing pressure. A capacitor Cres in parallel with the inductor coil 104 provides a resonant LC tank circuit. Each of these components, which are discussed in additional detail below, can be included within a hermetic housing 103 of the implantable device. The form factor of the housing 103 can depend upon where the implantable device 102 is intended to be implanted, but in general, the housing 103 will be quite small. One or more attachment mechanisms, not shown, can be connected to the housing 103 to hold the implantable device 102 in place and in its proper orientation once implanted in a patient.

In accordance with an embodiment, the rectifier 108, the power converter 112, the communication module 114, the serial interface 116, the RAM 122, the MCU 124, the sensor measurement circuitry 128, the timer(s) 126, and the temperature sensor 132 are all implemented within an application specific integrated circuitry (ASIC) 140, which can also be referred to as a sensor ASIC, since its primary function is to obtain sensor measurements and support communication capabilities that allow such sensor measurements to be provided to the external device 152.

In accordance with certain embodiments, the MCU 124 executes program code that is stored in memory 118 (e.g., the NVM 120 and/or RAM 122) of the implantable device 102 to thereby control operations of the implantable device 102. Such program code can be provided to the implantable device 102 and/or updated by the non-implantable device 152 or some other external device. The memory can also store diagnostic data, sensor measurements, etc. The serial interface 116 can be used by the MCU 124 to read and write to the NVM 120. The MCU 124 can, e.g., include one or more processors and/or a state machine.

The external device 152 (which can also be referred to as a non-implanted device 152) is shown as including an inductor coil 154, a driver 156, and a power supply 158. The power supply 158 can be, for example, a battery or circuitry that converts AC power received from an AC power outlet to DC power. The driver 156 (which can also be referred to as driver circuitry 156) can include circuitry that drives the inductor coil 154 with an AC signal for the purpose of recharging, powering and/or communicating with the implantable device 102. Accordingly, the driver 156 can, for example, include a DC-to-AC converter as well as communication circuitry. If used for communication, the driver 156 can be referred to as a telemetry or communication module. While not specifically shown, the external device 152 can also include a microcontroller unit (MCU), which can be part of or separate from the driver 156. In certain embodiments, the coil 154 is used to transmit AC power signals and communication signals to the implantable device 102, and a separate coil 164, coupled to a receiver 166, is used to receive communication signals from the implantable device. It would also be possible that a single coil (e.g., 154) be used for sending power signals to the implantable device and both transmitting and receiving communication signals to/from the implantable device 102. Additionally, the external device 152 can include further components or modules, such as a user interface, e.g., a graphical user interface (GUI), but not limited thereto. Since embodiments of the present invention primarily relate to the implantable device 102, not the external device 152, significant additional details of the external device 152 are not provided.

Referring again to the implantable device 102 shown in FIG. 1, the rectifier 108 and the energy storage capacitor Cpw collectively make up an energy harvest module 106. The rectifier 108, which is coupled between the inductor coil 104 and the storage capacitor Cpw, converts AC power signals, received from the non-implanted device 152, to DC signals that are used to charge the storage capacitor Cpw. (The letters "pw" refers to the term "power", because the storage capacitor Cpw is used to power active circuitry of the implantable device 102.) The rectifier 108 can be, e.g., a half-wave rectifier or a full-wave rectifier. In accordance with certain embodiments, the rectifier 108 is a voltage multiplier, such as, but not limited to, a voltage doubler. Other variations are also possible and within the scope of the embodiment described herein. The power converter 112 is used to convert the voltage stored on the storage capacitor Cpw to one or more appropriate voltage levels that are used to power the various different types of active circuitry of the implantable device 102. Depending upon implementation, the power converter 112 can output a single voltage, or can output two or more voltages. Depending upon implementation, the power converter 112 can include a step-down converter and/or a step-up converter, depending upon the voltage stored on the storage capacitor Cpw and the voltage(s) need to power the various different types of active circuitry of the implantable device.

As noted above, the capacitor Cres is in parallel with the inductor coil 104 to provide a resonant LC tank circuit. (The letters "res" refers to the term "resonance", because the capacitor Cres is used to specify a resonant frequency of the LC tank circuit.) This enables an appropriate resonant frequency to be selected to maximize the transfer of energy from the non-implanted device 152 to the implantable device 102, as well as to select an appropriate frequency allocated for use within the industrial, scientific and medical (ISM) radio band. For an example, the LC tank circuit (including the inductor coil 104 and the capacitor Cres) can be designed to have a resonant frequency of 6.78 MHz, but is not limited thereto.

The implantable device 102 does not include a battery, and more specifically, does not include (i.e., is devoid of) an electrochemical cell for powering the active circuitry of the implantable device 102. Rather, energy provided to and stored on the storage capacitor Cpw is used to power the active circuitry of the implantable device 102 when the external device 152 is within close proximity to (e.g., within about 6 inches of) the implantable device 102. This avoids certain problems associated with an implantable device including a battery. As noted above, a problem with an implantable device having a non-rechargeable battery is that the device is rendered inoperable once the battery is dead. A problem with an implantable device having a rechargeable battery is that the rechargeable battery will eventually get to the point that it can no longer be charged due to changes in the one or more electrochemical cells of the rechargeable battery. Accordingly, a battery powered implantable device eventually has to be explanted and replaced within a new implantable device after its battery dies, or the inoperable device is left implanted in the patient, both of which options are undesirable. In contrast to a battery powered implantable device, the implantable device 102 could remain implanted within a patient and operational for the entire life of the patient, never requiring removal or replacement.

The communication module 114 of the implantable device 102 can be used to detect and demodulate communication signals received via the inductor coil 104 from the external device 152. Additionally, the communication module 114 can be used to modulate and transmit communication signals via the inductor coil 104 to the external device 152. Exemplary modulation schemes that can be used for such communication include, but are not limited to, single frequency on-off keying (OOK), two frequency binary frequency-shift-keying (FSK), phase-shift-keying (PSK) modulation, or amplitude-shift keying (ASK).

The serial interface 116 provides access to the NVM 120 to enable data to be serially written to and read from the NVM 120. The MCU 124, which can include one or more processors and/or a state machine, is used to control the overall operation of the implantable device 102, including obtaining sensor measurements, reading and writing data to the RAM 122 and NVM 120, and controlling the communications performed by the communication module 114. The bus 110 can be used to enable the various components of the implantable device 102 that are coupled to the bus 110 to communicate with one another.

In accordance with an embodiment, the implantable device 102 is used to measure pressure within a cardiac region. For example, if the implantable device 102 is implanted in a patient's pulmonary artery, then the implantable device 102 can be used to measure pulmonary artery pressure (PAP). For another example, if the implantable device 102 is implanted in a patient's left atrium, then the implantable device 102 can be used to measure left atrial pressure (LAP).

In accordance with an embodiment, the pressure sensor comprises a capacitor Cpr whose capacitance changes with changes in pressure, and thus, is indicative of pressure. Accordingly, the capacitor Cpr can be referred to as a pressure sensing capacitor Cpr. (The letters "pr" refers to the term "pressure", because the capacitor Cpr is used to measure pressure.) Unlike the other components of implantable device 102, at least a portion of pressure sensing capacitor Cpr may be exposed to the environment surrounding the implantable device 102 to facilitate accurately measuring the pressure in the environment. More specifically, the capacitor Cpr can include two plates that are spaced apart from one another. One of the plates of the capacitor Cpr can be positioned on an inner surface of a deflectable region of a housing or body (e.g., 103) of the implantable device 102, and the other plate of the capacitor Cpr can be supported on a stiff non-deflectable substrate. The capacitance of the capacitor Cpr is dependent upon the gap or distance between the two plates of the capacitor Cpr. Changes in pressure will cause a displacement of the deflectable region of the housing or body (e.g., 103) of the implantable device 102, and thus, will cause a displacement of the plate of the capacitor Cpr that is positioned on the inner surface of the deflectable region. This changes the capacitance of the capacitor Cpr, thereby enabling the capacitor Cpr to be used as a pressure sensing capacitor. As will be described in additional detail below, with reference to FIG. 2, the sensor measurement circuitry 128 (which is an example of active circuitry powered using energy stored on the storage capacitor Cpw) can be used to convert such analog pressure measurements to digital pressure measurements.

The implantable device 102 can also be used to measure core body temperature using the temperature sensor 132. The temperature sensor 132 can be, e.g., an integrated circuit (IC) temperature sensor including one or more diode devices that are used to produce a first base-to-emitter voltage drop (VBE1) and a second base-to-emitter voltage drop (VBE2), which are complimentary to absolute temperature (CTAT), and used to determine a $\Delta VBE=VBE2-VBE1$, which is proportion to absolute temperature (PTAT), as is known in the art. Alternatively, the temperature sensor 132 can include a thermistor. Either way, the temperature sensor 132 will include at least some active circuitry that is used to produce digital temperature measurements.

One or more other types of sensors can be included in the implantable device 102 and can include active circuitry that is powered using energy stored on the storage capacitor Cpw. For example, the implantable device can also include a venous oxygen saturation (SvO2) sensor, or a blood glucose sensor, just to name a few.

The active circuitry of the implantable device 102 (which is powered using the energy stored on the storage capacitor Cpw) can include one or more of the communication module 114, the serial interface 116, the NVM 120, the RAM 122, the MCU 124, the sensor measurement circuitry 128, and/or the temperature sensor 132, but is not limited thereto. All of the various different types of active circuitry can be powered at the same time, or certain active circuitry can be powered at different times than other types.

In accordance with certain embodiments of the present technology, during "burst" periods, the storage capacitor Cpw is used to accumulate and store energy received via the inductor coil 104 from the non-implanted device 152, and during "quiet" periods that are interleaved with the "burst" periods (during which energy is not received from the non-implanted device 152), active circuitry of the implantable device 102 (which is powered by the energy stored on the storage capacitor Cpw) is used to perform one or more of a plurality of predetermined operations of the implantable device 102. Such predetermined operations include, but are not limited to, obtaining a sensor measurement from a sensor of the implantable device, transmitting a communication signal (e.g., including a sensor measurement) to the non-implanted device, and receiving a communication signal from the non-implanted device. Additional details of these features of the present technology are described below with reference to FIGS. 3-5.

Figure 2:
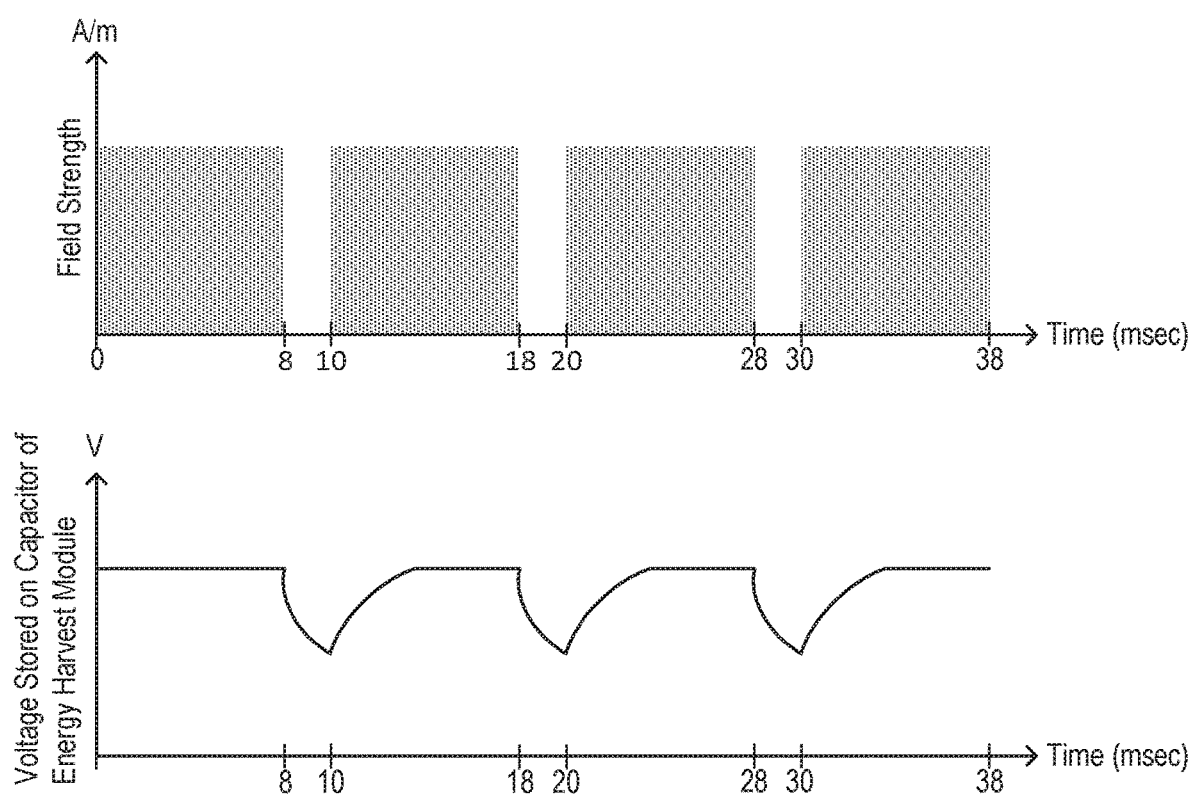
FIG. 2 includes an upper graph that illustrates how a burst field strength is provided to and received by the implantable device varies over time, and a lower graph that illustrates how a voltage stored on a storage capacitor of the implantable device, which is used to power active circuitry thereof, varies over time.

FIG. 2 includes an upper graph that illustrates how a burst field strength that is provided by the non-implanted device 152 to (and received by) the implantable device 102 varies over time. The lower graph in FIG. 2 illustrates how the voltage stored on the storage capacitor Cpw of the implantable device 102 (which is used to power active circuitry of the implantable device 102) varies over time. In accordance with an embodiment, the storage capacitor Cpw can store about 5 Volts (V) and is configured to be fully charged at the end of each burst period. In accordance with an embodiment, at the end of each quiet period at least a minimum amount of voltage, e.g., at least 2V is still stored in the storage capacitor Cpw so that the MCU 124 of the implantable device 102 is still able to operate. The use of other fully charged and minimum voltage values is also possible and within the scope of the embodiments described herein.

Referring again to the upper graph in FIG. 2, bursts of energy are shown as being provided from the non-implanted device 152 to the implantable device 102 for 8 milliseconds (ms) at a time, with 2 ms periods of time during which no energy is provided interleaved therebetween. In other words, each of the burst periods is shown as being 8 ms in length, and each of the quiet periods is shown as being 2 ms in length. The magnetic field strength of such bursts, that are transmitted by the non-implanted device 152 to the implantable device 102, will be attenuated due to a distance between the non-implanted device 152 and the implantable device 102 and the patient tissue therebetween. Accordingly, the magnetic field strength of such bursts when received by the implantable device 102 can be relatively low, e.g., on the order of about 0.5 to 2.5 Nm, but are not limited thereto. The use of lower or higher magnetic field strength bursts are also possible and within the scope of the embodiments described herein.

The periods of time during which bursts of energy are provided from the non-implanted device 152 to the implantable device 102 can be referred to herein as burst periods, energy harvest periods, or more generally, first periods of time. As can be appreciated from the upper graph in FIG. 2, consecutive burst periods are shown as being separated from one another by periods of time during which bursts of energy are not provided from the non-implanted device 152 to the implantable device 102. The periods of time during which bursts of energy are not provided from the non-implanted device 152 to the implantable device 102 can be referred to herein as energy quiet periods, quiet periods, or more generally, second periods of time. In FIG. 2, each of the burst periods (aka energy harvest periods or first periods of time) is shown as being 8 ms, and each of the quiet periods (aka quiet energy periods or second periods of time) is shown as being 2 ms. More generally, in accordance with certain embodiments each of the burst periods is within the range of 5 to 15 ms, inclusive, and each of the quiet periods is within the range of 1 to 4 ms, inclusive. The user of longer or shorter burst periods and/or quiet periods are also possible. Since it will typically take longer to charge the energy storage capacitor Cpw than it will to obtain sensor measurements and/or transmit communication signals, the burst periods are preferably longer than the quiet periods, e.g., 2× or 4× longer, but that need not be the case in alternative embodiments.

During the burst periods (aka the energy harvest periods or first periods of time) the non-implantable device 152 transmits AC power signals to the implantable device 102, the inductor coil 104 of the implantable device 102 receives the AC power signals from the non-implanted device 152, and the rectifier 108 of the implantable device 102 converts the AC power signals to DC signals that are used to charge the storage capacitor Cpw. In accordance with certain embodiments, the non-implantable device 152 generates the AC power signals by using the driver 156 to drive the inductor coil 154 with a relatively large AC current. Such an AC power signal is represented in FIG. 1 by the arrowed line labeled 172.

During the quiet periods (aka the energy quiet periods or second periods of time), which are interleaved with the burst periods, the non-implanted device 152 does not transmit AC power signals, and thus, the implantable device 102 does not receive AC power signals from the non-implanted device 152. Rather, during the quiet periods, the active circuitry of the implantable device 102, which is powered by the energy stored on the storage capacitor Cpw, is used to perform at least one of a plurality of predetermined operations of the implantable device 102. In accordance with certain embodiments, such predetermined operations (that the implantable device can perform during the quiet periods) include obtaining a pressure sensor measurement from the pressure sensor Cpr of the implantable device 102, transmitting a communication signal (e.g., including a sensor measurement) to the non-implanted device 152, and receiving a communication signal from the non-implanted device 152. Such a communication signal that is transmitted from the non-implanted device 152 to the implantable device 102, and received by the implantable device 102, is represented by the arrowed line labeled 174. Such a communication signal that is transmitted from the implantable device 102 to the non-implanted device 152, and received by the non-implanted device 152, is represented by the arrowed line labeled 176. Additional or alternative types of sensor measurements, e.g., temperature sensor measurements, can be obtained during quiet periods and/or transmitted to the non-implanted device 152 in communication signals during the quiet periods.

In accordance with certain embodiments of the present technology, the same inductor coil 104 (of the implantable device 102) that is used to receive the AC power signals during the burst periods is used to transmit and/or receive communication signals during the quiet periods. This helps make the implantable device 102 sufficiently small enough to be placed in a pulmonary artery or other relatively small location. During the quiet periods, the inductor coil 104 of the implantable device 102 does not receive AC power signals from the non-implanted device 152. Beneficially, communications signals (174 and/or 176) transmitted between the implantable device 102 and the non-implanted device 152 are thereby subject to less noise compared to if the communications signals were transmitted at the same times that the inductor coil 104 of the implantable device 102 received AC power signals from the non-implanted device 152. Additionally, by having the implantable device 102 obtain physiologic sensor measurements (e.g., pressure sensor measurements) during the quiet periods, such measurements are subject to less noise compared to if the measurements were obtained at the same times that the implantable device 102 received AC power signals from the non-implanted device 152.

The non-implanted device 152 can use the same inductor coil 154 to send AC power signals (172) to the implantable device 102 as it does to transmit and receive communication signals (174 and/or 176) from the implantable device 102. Alternatively, because the non-implanted device 152 does not have the same size and complexity constraints as the implantable device 102, the non-implanted device 152 can use a different inductor coil to send AC power signal to the implantable device 102 than it does to transmit and receive communication signals from the implantable device 102. As noted above, in certain embodiments, the coil 154 is used to transmit AC power signals and communication signals to the implantable device 102, and a separate coil 164, coupled to a receiver 166, is used to receive communication signals from the implantable device. Other variations are also possible and within the scope of the embodiments described herein.

As noted above, during quiet periods (aka the energy quiet periods or second periods of time), communication signals can be transmitted between the non-implantable device 152 and the implantable device 102, in either direction. In accordance with certain embodiments of the present technology, the field strength of such communication signals (transmitted and received during the quiet periods) is at least 10× (and potentially at least 100×) less than the field strength of the power signals transmitted from the non-implanted 152 to the implantable device 102 during the burst periods. This is one manner in which the implantable device 102 can distinguish communication signals from power signals. Accordingly, if an emitted magnetic field strength of an AC power signal is about 30 Nm, then an emitted magnetic field strength of a communication signal can be on the order of 3 Nm, or even as low as about 0.3 Nm, but is not limited thereto.

As can be appreciated from the lower graph of FIG. 2, during each quiet period some of the energy that is stored on the storage capacitor Cpw is depleted because it is used to power active circuitry of the implantable device 102 to obtain one or more pressure measurements and/or perform communications. As can also be appreciate from the lower graph of FIG. 2, during each burst period the energy that had been dissipated during the preceding quiet period is replaced, preferably, so that the storage capacitor Cpw is fully charged at the end of each burst period, but that may not always be the case.

Figure 3:
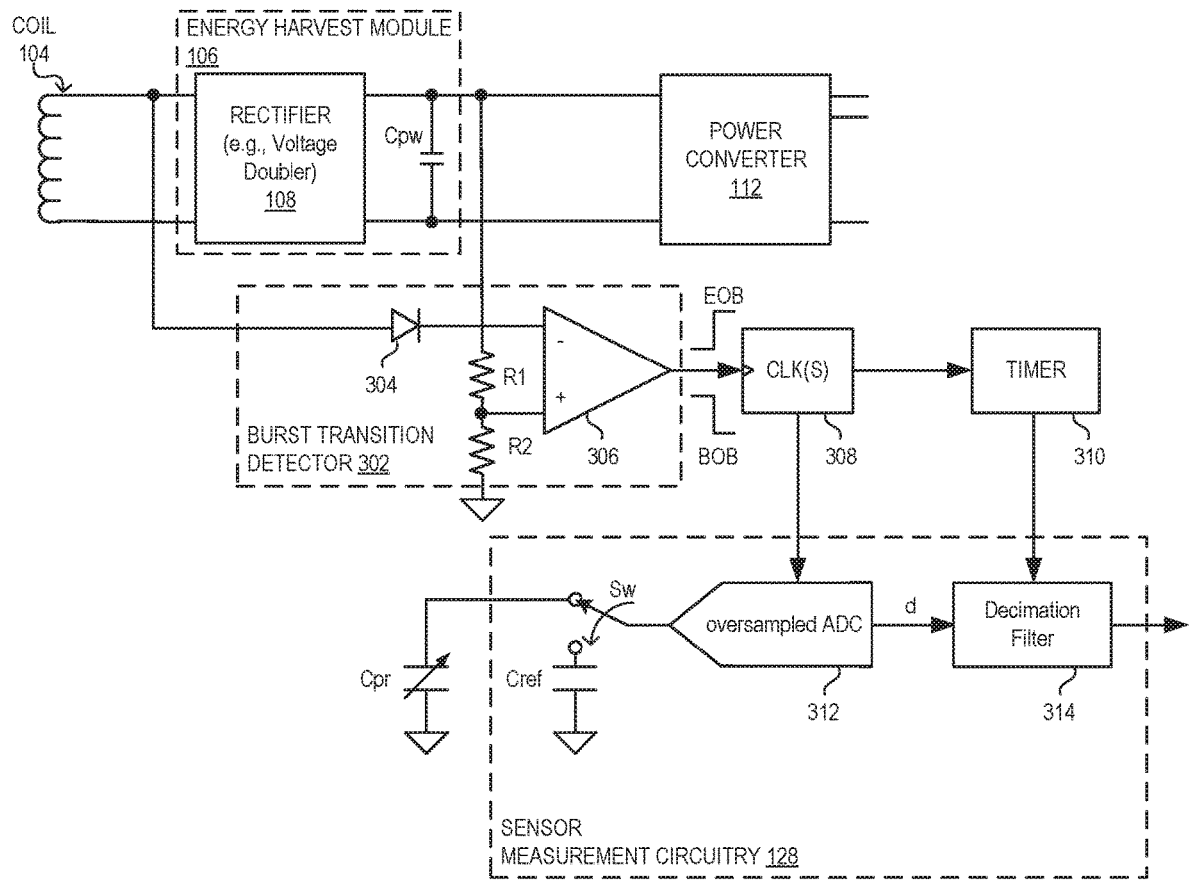
FIG. 3 illustrates additional details of a portion of the implantable device introduced in FIG. 1.

FIG. 3 illustrates additional details of a portion of the implantable device introduced in FIG. 1. More specifically, FIG. 3 illustrates that active circuitry of the implantable device 102 can include a burst transition detector 302 that can be used to detect the end of each burst period, and thus, the start of each quiet period (aka second period of time). This enables the implantable device 102 to know when it is able to obtain one or more sensor measurements and/or perform communications in the absence of noise caused by the AC power signals transmitted during the burst periods (aka first periods of time). The burst transition detector 302 is shown as including a diode 304, resistors R1 and R2, and an operational amplifier (op-amp) 306 that is connected as a comparator. The anode of the diode 304 is connected to a terminal of the inductor coil 104, and the cathode of the diode 304 is connected to the inverting (−) input terminal of the op-amp 306. The resistors R1 and R2 are connected as a voltage divider to provide a reference voltage to the non-inverting (+) input of the op-amp, and a voltage at the cathode of the diode 304 is provided to the inverting (−) input of the op-amp 306. The output of the op-amp 306 will go HIGH whenever the voltage on the cathode of the diode 304 falls below the reference voltage provide by the voltage divider. This triggers one or more clocks 308 and/or timers 310, which in turn causes an oversampled analog to digital converter (ADC) 312 to sample the voltage stored on the capacitor Cpr (which is indicative of pressure), and a decimation filter 314 to filter an output of the ADC 312, such that an output of the sensor measurement circuitry 128 is indicative of the pressure sensed by the capacitor Cpr. Such a sensor measurement can be temporarily stored in memory (e.g., RAM 122 and/or NVM 120) before being transmitted to the non-implanted device 152 during the same quiet period, or during a later quiet period. It may also be possible for a sensor measurement to be obtained by the sensor measurement circuitry 128 and transmitted by the communication module 114 and inductor coil 104 to the non-implanted device 152 during a single (i.e., same) quiet period.

More generally, the burst transition detector 302 can be configured to output an end-of-burst (EOB) signal when it detects a transition from a burst period to a quiet period. Additionally, the burst transition detector 302 can output a beginning-of-burst (BOB) signal when it detects a transition from a quiet period to a burst period. In the embodiment shown, the EOB and BOB signals are produced at the output of the op-amp 306, and the EOB signal is produced when the output of the op-amp 306 transitions from LOW to HIGH, and the BOB signal is produced when the output of the op-amp 306 transitions from HIGH to LOW. Other variations are also possible and within the embodiments of the present technology described herein.

Still referring to FIG. 3, the sensor measurement circuitry 128 is also shown as including a reference capacitor Cref and a switch Sw. The switch Sw, under the control of the MCU 124, is used to either connect the capacitive pressure sensor Cpr or the reference capacitor Cref to the input of the ADC 312. As noted above, the capacitive pressure sensor Cpr is configured such that its capacitance should change with changes in the pressure (e.g., PAP) being measured. By contrast, the reference capacitor Cref is configured such that its capacitance is not affected by (i.e., is independent of) changes in the pressure (e.g., PAP) being measured, and such that any changes in measurements of the capacitance of the reference capacitor Cref are indicative of drift of the active circuitry (e.g., the ADC 312) of the sensor measurement circuitry 128. Drift is a phenomenon where operation of the ADC 312 (and/or other active circuitry) changes not because of a change to the input to the ADC, but rather due to changes to circuit elements resulting from aging and/or changes in temperature.

In accordance with certain embodiments of the present technology, from time-to-time (e.g., in response to a triggering event, such as the voltage stored on the capacitor Cpw crossing a threshold), the ADC 312 can be used to measure the capacitance of the reference capacitor Cref, and such measurements can be stored, e.g., in the NVM 120. To improve the accuracy of pressure sensor measurements, the MCU 124 can identify changes to the measured capacitance of the reference capacitor Cref, and can apply a drift error correction factor to pressure sensor measurements (obtained using the capacitive pressure sensor Cpr and the ADC 312). Alternatively, the measured capacitance of the reference capacitor Cref, or a drift error correction factor determined based thereon, can be transmitted from the implantable device 102 to the non-implantable device 152 to enable the non-implanted device 152 (or some other system in communication with the non-implanted device 152) to apply a drift error correction to pressure sensor measurements. While only one reference capacitor Cref is shown in FIG. 3, it is also possible that multiple reference capacitors (e.g., two, three, or more) be included, and that the switch Sw is used to select a specific one (or multiple ones) of the reference capacitors to connect the input of the ADC to better detect drift in the active circuitry, and apply one or more drift error correction factors to pressure sensor measurements (obtained using the capacitive pressure sensor Cpr and the ADC 312). For example, a ratio between an initial reference capacitor measurement and a present reference capacitor measurement can be applied to a present pressure sensor capacitor measurement as a scaling factor to compensate the drift error. Other variations are also possible and within the scope of the embodiments disclosed herein.

Additionally, to improve accuracy, sensor measurements (e.g., pressure sensor measurements) obtained by the implantable device may need to be calibrated for non-linearity and/or offset. In accordance with certain embodiments, non-linearity calibration data and offset calibration data are stored in the NVM 120 and can be used by the implantable device 102 to calibrate sensor measurements before they are transmitted from the implantable device 102 to the non-implantable device 152. Alternatively, the non-linearity calibration data and offset calibration data (stored in the NVM 120) can be transmitted from the implantable device 102 to the non-implantable device 152 to enable the non-implanted device 152 (or some other system in communication with the non-implanted device 152) to calibrate sensor measurements (transmitted from the implantable device 102 to the non-implanted device 152) external to the implantable device 102. The non-linearity calibration data can be determined prior to implant of the implantable device 102, e.g., during or after manufacture thereof, and the offset calibration data can be determined, e.g., after implant of the implantable device 102 into a patient. For a more specific example, after the implantable device 102 is implanted in a patient's pulmonary artery, a PAP measurement can be obtained using the implantable device and calibrated to compensate for a non-linearity of the sensor. This calibrated measurement can be compared to a PAP measurement obtained using the standard pulmonary artery catheterization (PAC) method in order to determine an offset, and calibration offset data can be transmitted to the implantable device and stored in its NVM 120 to provide for later access to such calibration data. Other variations are also possible.

Figure 4:
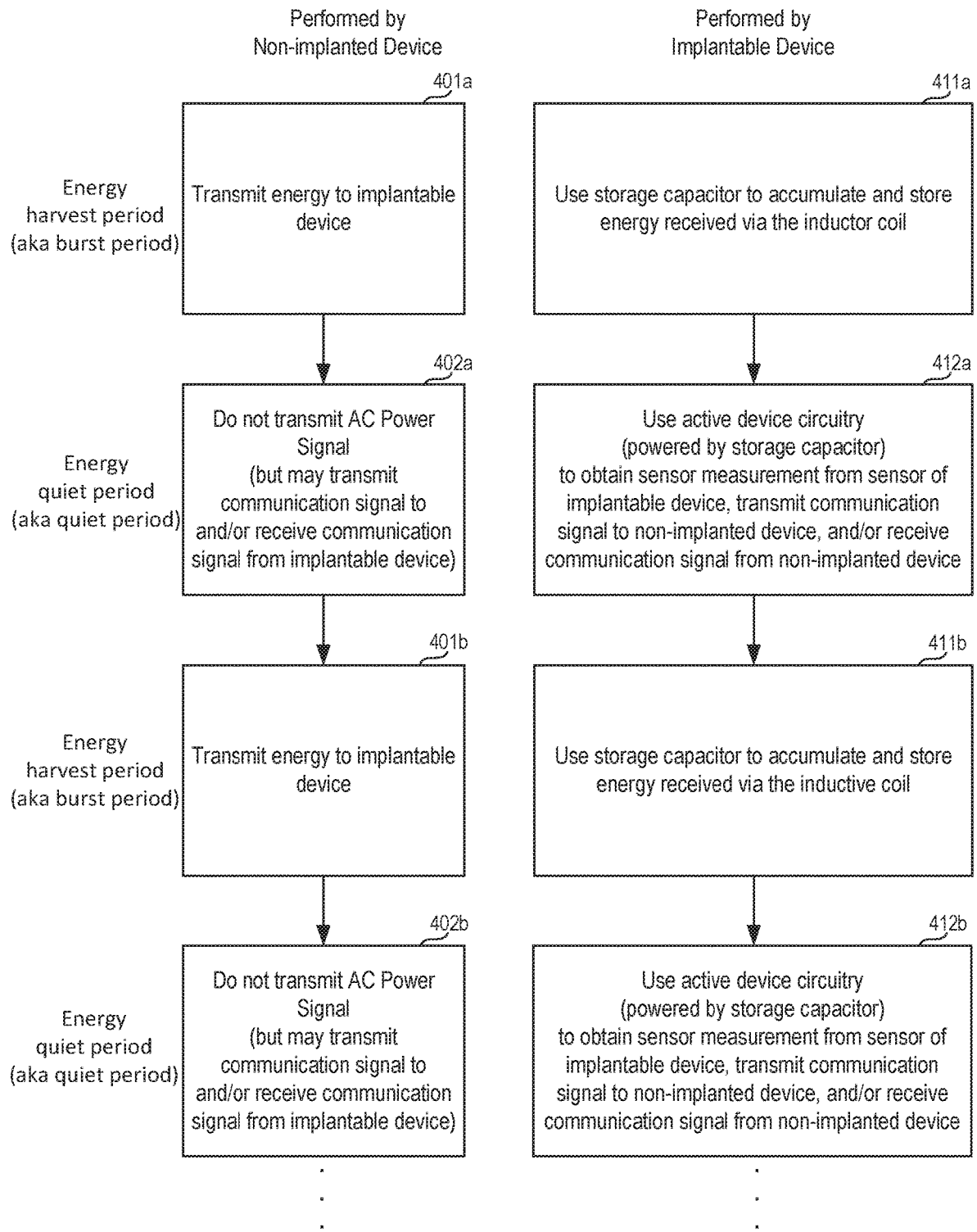
FIG. 4 illustrates how the non-implanted device and implantable device, introduced above in FIG. 1, perform various steps in parallel with one another, in accordance with certain embodiments of the present technology.

FIG. 4 illustrates how the non-implanted device 152 and the implantable device 102, introduced above in FIG. 1, can perform various steps in parallel with one another, in accordance with certain embodiments of the present technology. In FIG. 4, the steps along the left are steps performed by the non-implanted device 152, and the steps along the right are steps performed by the implantable device 102 after implantation into a patient. Referring to FIG. 4, at step 401a the non-implanted device 152 transmits energy to the implantable device 102, and in parallel at step 411a the implantable device 102 uses its storage capacitor Cpw to accumulate and store energy received via its inductor coil 104. Step 411a can also involve the rectifier 108 converting an AC power signal, received from the non-implanted device 152, to a DC signal.

At step 402a the non-implanted device does not transmit energy to the implantable device 102, and in parallel at step 412a the implantable device uses its active circuitry (powered by storage capacitor Cpw) to obtain one or more sensor measurements (e.g., a pressure and/or temperature measurement) from one or more sensors (e.g., the Cpr and/or temperature sensor 132) of the implantable device 102, transmit a communication signal to the non-implanted device 152, or receive a communication signal from the non-implanted device 152. A communication signal transmitted from the implantable device 102 to the non-implanted device 152 can include one or more sensor measurements, calibration data, patient identifier data, device identifier data, and/or the like, but is not limited thereto. A communication signal transmitted from the non-implanted device 152 to the implantable device 102 can provide instructions to the implantable device 102 and/or cause the implantable device 102 to store certain calibration data in its NVM 120, but is not limited thereto. Additional instances of steps 401, 411, 402, and 412 are labeled 410b, 411b, 402b, and 412b in FIG. 4.

Figure 5:
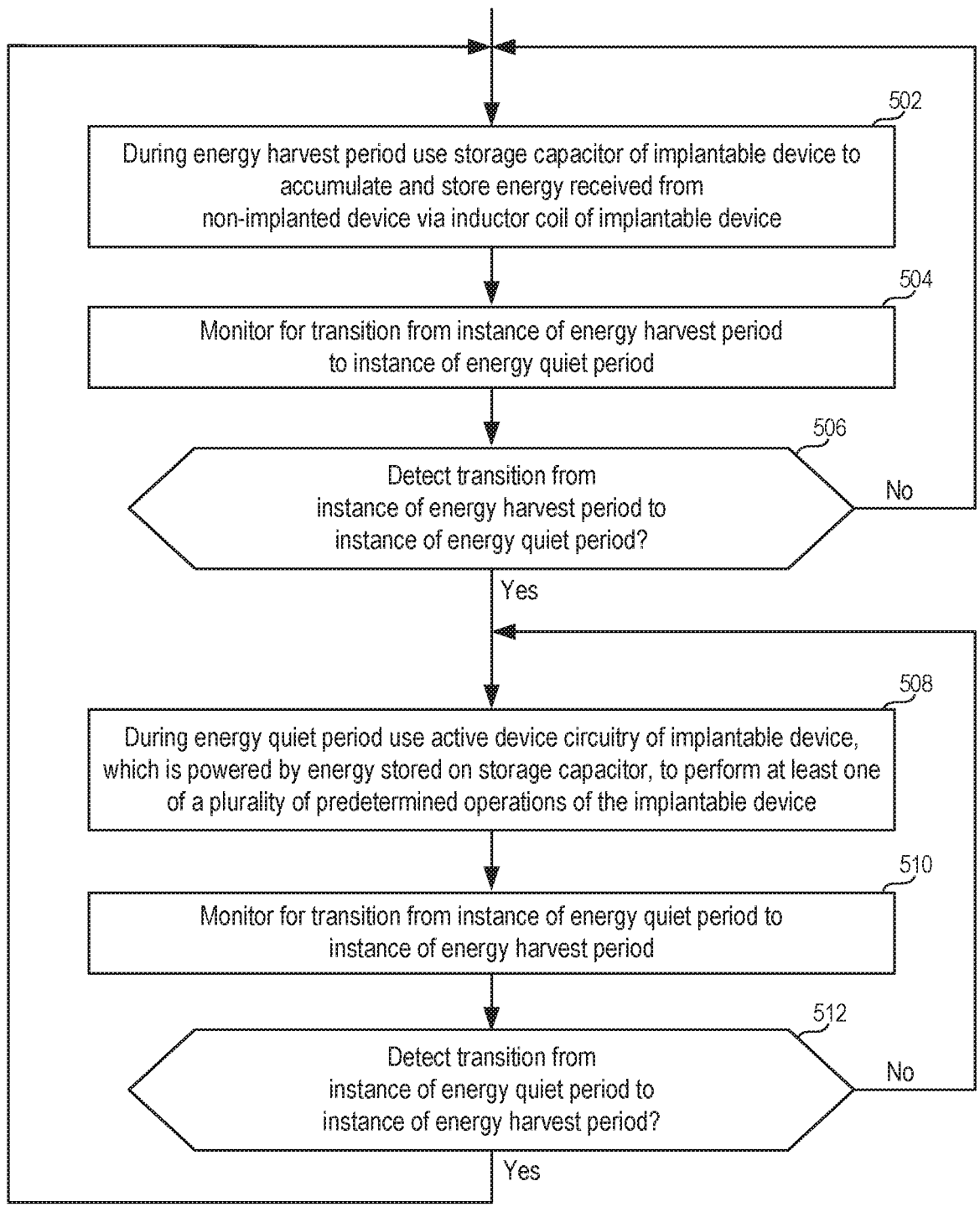
FIG. 5 is a high level flow diagram that is used to summarize methods according to various embodiments of the present technology.

FIG. 5 is a high level flow diagram that is used to summarize methods according to various embodiments of the present technology. Referring to FIG. 5, at step 502, during an energy harvest period, a storage capacitor (e.g., Cpw) of an implantable device (e.g., 102) is used to accumulate and store energy received, via an inductor coil (e.g., 104) of the implantable device, from a non-implanted device (e.g., 152). As noted above, the energy harvest period can also be referred to as a burst period or a first period of time.

Still referring to FIG. 5, at step 504 the implantable device (e.g., 102) monitors for a transition from an instance of the energy harvest period to an instance of an energy quiet period. The burst transition detector 302, described above with reference to FIG. 3, is an example of circuitry that can be used to perform step 504. As noted above, the energy quiet period can also be referred to as a quiet period or a second period of time.

At step 506 there is a determination of whether a transition from an instance of the energy harvest period to an instance of an energy quiet period is detected. If the answer to the determination at step 506 is No, the flow returns to step 502. If the answer to the determination at step 508 is Yes, then flow goes to step 508.

At step 508, during an energy quiet period active circuitry of the implantable device, which is powered by energy stored in the storage capacitor, is used to perform at least one of a plurality of predetermined operations of the implantable device, examples of which were described above, and thus, need not be repeated.

At step 510, the implantable device monitors for a transition from an instance of the energy quiet period to an instance of the energy harvest period. The burst transition detector 302, described above with reference to FIG. 3, is an example of circuitry that can be used to perform step 510.

At step 512 there is a determination of whether a transition from an instance of the energy quiet period to an instance of an energy harvest period is detected. If the answer to the determination at step 512 is No, the flow returns to step 508. If the answer to the determination at step 512 is Yes, then flow returns to step 502. The steps described with reference to FIG. 5 can continue so long as the non-implanted device is within proximity of and periodically transmitting power signals to the implantable device, which overall or collective period can be referred to as a power and interrogation period.

Certain embodiments of the present technology described herein can be used to enable high-resolution pulmonary artery pressure (PAP) measurements, as well as other types of pressure measurements, to be obtained using a chronic implantable device that does not include a battery. The normal range of PAP is from about 10 to 30 mmHg with a mean of approximately 25 mmHg. In accordance with certain embodiments, PAP measurements obtained using the implantable device 102 have a sensitivity of less than 1 mmHg. In accordance with certain embodiments, to achieve a sensitivity of 1 mmHg, the active circuitry of the implantable device is preferably capable of resolving a change of less than 650 aF (650×10-18 F), where F is Farad. Obtaining pressure (e.g., PAP) sensor measurements during quiet periods helps to achieve such a desired high level of accuracy. Further, the use of one or more reference capacitors to compensate for drift in active circuitry, e.g., due to aging and/or temperature variations of circuit elements, also helps to achieve such a desired high level of accuracy.

In accordance with certain embodiments of the present technology, the housing of the implantable device 102 and the capacitor Cpr are physically small enough to be able to fit into a pulmonary artery.

In certain embodiments, such as those described above with reference to FIG. 2, the burst periods always have the same length of time, and the quiet periods always have the same length of time. In accordance with alternative embodiments, lengths of the burst periods can vary over time, and/or lengths of the quiet periods can vary over time. The quiet periods can be a function of the amount of energy consumed by the active circuitry (e.g., including the capacitive pressure sensor Cpr and the sensor measurement circuitry 128) during the quiet periods as well as the size of the storage capacitor Cpw. Due to the limited size of the implantable device, the size of the storage capacitor Cpw is limited. Due to these limitations the quiet period is likely on the order of a few milliseconds, but is not limited thereto. In FIG. 1 the storage capacitor Cpw is shown as a single capacitor, but it can be made up two or more capacitors, which can be connected in series and/or in parallel, depending upon specific implementation.

In accordance with certain embodiments, the capacitive pressure sensor Cpr is hermetically sealed with a thin layer of glass that is used to deflect one plate of the capacitor based on pressure. This creates a very small change in capacitance. Due to size limitations of the capacitive pressure sensor and the parasitic capacitance of the capacitive pressure sensor to electronics, the baseline capacitance may be a few pF, nominally 2 pF. Where the desire is to sense a 650 aF change from a 2 pF, this involves resolving about 1 in 3000, thus, at least a 13-bit signal-to-noise ratio (SNR). To achieve such performance, the ADC 312 discussed above with reference to FIG. 3 can be implemented as a sigma-delta data converter, which has good SNR performance.

In accordance with certain embodiments, communications can be triggered based on when the external device stops transmitting energy. When this happens, an EOB signal can be created by a burst transition detector (e.g., 302 in FIG. 3). After an initialization period, this can trigger the starting of sending data from the implantable device to the non-implanted device. This can also start one or more clocks that are used to oversample an ADC (e.g., 312 in FIG. 3), e.g., as can be appreciated from FIG. 3. In accordance with certain embodiments, the clock(s) (e.g., 308 in FIG. 3) run at frequencies fast enough to oversample the data and to perform a capacitance to voltage conversion within a quiet period. Additional timer(s) (e.g., 310 in FIG. 3) can be used to decimate the ADC signal to a final sample rate of interest. Lowpass filters can be used to filter out unwanted signals during the decimation process. In accordance with certain embodiments, timer(s) 310 are used to ensure the ADC 312 and filter 314 have enough time to settle before latching a valid conversion value.

Embodiments of the present technology have been described above with the aid of functional building blocks illustrating the performance of specified functions and relationships thereof. The boundaries of these functional building blocks have often been defined herein for the convenience of the description. Alternate boundaries can be defined so long as the specified functions and relationships thereof are appropriately performed. Any such alternate boundaries are thus within the scope and spirit of the claimed invention.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the embodiments of the present technology without departing from its scope. While the dimensions, types of materials and coatings described herein are intended to define the parameters of the embodiments of the present technology, they are by no means limiting and are exemplary embodiments. Many other embodiments will be apparent to those of skill in the art upon reviewing the above description. The scope of the embodiments of the present technology should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means—plus-function format and are not intended to be interpreted based on 35 U.S.C. § 112(f), unless and until such claim limitations expressly use the phrase "means for" followed by a statement of function void of further structure.

What is claimed is:

1. A method for use by an implantable device that includes an inductor coil, a storage capacitor, active circuitry, and a sensor, but does not include an electrochemical cell for powering the active circuitry, the method comprising:
   during first periods of time, using the storage capacitor to accumulate and store energy received from a non-implanted device via the inductor coil; and
   during second periods of time that are interleaved with the first periods of time and during which energy is not received from the non-implanted device, using the active circuitry of the implantable device, which is powered by the energy stored on the storage capacitor, to perform at least one of a plurality of predetermined operations of the implantable device;
   wherein the plurality of predetermined operations comprises obtaining a sensor measurement from the sensor of the implantable device, transmitting a communication signal including the sensor measurement to the non-implanted device, and receiving a communication signal from the non-implanted device;

wherein during the first periods of time the inductor coil of the implantable device receives AC power signals from the non-implanted device, and the implantable device converts the AC power signals to DC signals that are used to charge the storage capacitor of the implantable device;

wherein during at least some of the second periods of time, the active circuitry of the implantable device is used to obtain sensor measurements from the sensor of the implantable device; and wherein during the second periods of time the inductor coil of the implantable device does not receive AC power signals from the non-implanted device, and thus, communications signals transmitted between the implantable device and the non-implanted device are subject to less noise compared to if the communications signals were transmitted at the same times that the inductor coil of the implantable device receives AC power signals from the non-implanted device, and sensor measurements obtained from the sensor of the implantable device are subject to less noise compared to if the sensor measurements were obtained from the sensor of the implantable device at the same times that the inductor coil of the implantable device receives AC power signals from the non-implanted device.

2. The method of claim 1, wherein:
the implantable device also includes memory configured to store one or more sensor measurements therein, and wherein the sensor measurement that is transmitted to the non-implanted device in a communication signal is stored in the memory prior to being transmitted to the non-implanted device.

3. The method of claim 1, wherein:
the same inductor coil of the implantable device, which is used to receive energy from the non-implanted device during the first periods of time, is also used for the transmitting and the receiving of the communications signals to and from the non-implanted device during at least some instances of the second periods of time.

4. The method of claim 1, wherein the sensor comprises a passive capacitive pressure sensor whose capacitance changes with changes in pressure and is thereby indicative of pressure, and the method further comprises:
using the active circuitry to obtain sensor measurements from the passive capacitive pressure sensor and convert the sensor measurements from analog measurements to digital measurements that are stored in memory and/or transmitted in one or more communication signals from the implantable device to the non-implanted device.

5. The method of claim 4, wherein the implantable device includes one or more reference capacitors, and the method further comprises:
using the active circuitry to obtain reference capacitance measurements of at least one of the one or more reference capacitors and convert the reference capacitance measurements from analog measurements to digital measurements that are stored in memory and/or transmitted in one or more communication signals from the implantable device to the non-implanted device;
wherein changes over time in the reference capacitance measurements are indicative of drift in the active circuitry; and wherein the reference capacitance measurements are used by the implantable device, or the non-implanted device, to compensate for the drift in the active circuitry.

6. The method of claim 4, wherein the implantable device is configured to be implanted in a pulmonary artery, and wherein the sensor measurements obtained using the sensor are indicative of pulmonary artery pressure (PAP).

7. The method of claim 4, further comprising:
the implantable device detecting a transition from an instance of the first period of time to an instance of the second period of time, and in response thereto, triggering use of the active circuitry configured to obtain a sensor measurement from the passive capacitive pressure sensor and convert the sensor measurement from an analog measurement to a digital measurement.

8. The method of claim 1, wherein the implantable device includes non-volatile memory, and wherein the method further comprises storing device specific information in the non-volatile memory, the device specific information including:
a patient identifier indicative a patient in which the implantable device is implanted;
sensor linearity calibration data that is used to compensate for a non-linearity of the sensor of the implantable device; and
sensor offset calibration data that is used to compensate for an offset in pressure sensor measurements obtained using the sensor of the implantable device.

9. The method of claim 8, wherein:
during one or more instances of the second periods of time, the active circuitry causes transmitting of one or more communication signals including the device specific information from the implantable device to the non-implanted device.

10. A method for use by a system including an implantable device and a non-implanted device, wherein the implantable device includes an inductor coil, a storage capacitor, active circuitry, memory, and a sensor, but does not include an electrochemical cell for powering the active circuitry, the method comprising:
during first periods of time, the non-implanted device transmitting energy to the implantable device, and the implantable device using the storage capacitor thereof to accumulate and store energy received from the non-implanted device via the inductor coil of the implantable device; and
during second periods of time that are interleaved with the first periods of time, the non-implanted device not transmitting power signals to the implantable device, and the active circuitry of the implantable device, which is powered by the energy stored on the storage capacitor, performing at least one of a plurality of predetermined operations of the implantable device;
wherein the predetermined operations that the active circuitry of the implantable device performs during one or more instances of the second periods of time include:
receiving one or more communication signals from the non-implanted device;
obtaining one or more sensor measurements using the sensor of the implantable device; and
transmitting one or more communication signals including one or more of the sensor measurements from the implantable device to the non-implanted device;
wherein during at least some of the second periods of time, the active circuitry of the implantable device is used to obtain sensor measurements from the sensor of the implantable device; and wherein during the second periods of time, energy is not transmitted from the non-implanted device to the implantable device, and thus, sensor measurements obtained from the sensor of the implantable device are subject to less noise compared to if the sensor measurements were obtained from the sensor of the implantable device at the same times that energy is transmitted from the non-implanted device to the implantable device.

11. The method of claim 10, wherein:

during the first periods of time the inductor coil of the implantable device receives AC power signals from the non-implanted device, and the implantable device converts the AC power signals to DC signals that are used to charge the storage capacitor of the implantable device; and during the second periods of time the inductor coil of the implantable device does not receive AC power signals from the non-implanted device, and thus, communications signals transmitted between the implantable device and the non-implanted device are subject to less noise compared to if the communications signals were transmitted at the same times that the inductor coil of the implantable device receives AC power signals from the non-implanted device.

12. An implantable device, comprising:

a hermetic housing;

an inductor coil, a storage capacitor, active circuitry, a sensor, and memory all within the hermetic housing;

the active circuitry including a controller and a communication interface;

the controller configured to control other portions of the active circuitry including the communication interface;

the communication interface configured to enable wireless communication between the implantable device and a non-implanted device;

the implantable device devoid of an electrochemical cell for powering the active circuitry;

wherein the storage capacitor is configured to accumulate and store energy received from a non-implanted device via the inductor coil during first periods of time; and wherein the active circuitry of the implantable device, which is powered by the energy stored on the storage capacitor, is configured to perform at least one of a plurality of predetermined operations of the implantable device during second periods of time that are interleaved with the first periods of time;

wherein during one or more instances of the second periods of time, the operation performed by the active circuitry comprises obtaining one or more sensor measurements from the sensor of the implantable device and storing the one or more sensor measurements in the memory of the implantable device; and wherein during one or more further instances of the second periods of time, the operation performed by the active circuitry comprises transmitting one or more communication signals including one or more of the sensor measurements from the implantable device to the non-implanted device.

13. The implantable device of claim 12, wherein:

during one or more additional instances of the second periods of time, the operation performed by the active circuitry comprises receiving one or more communication signals from the non-implanted device.

14. The implantable device of claim 13, wherein:

the same inductor coil of the implantable device, which is used to receive energy from the non-implanted device during the first periods of time, is also used for the transmitting and the receiving of the communications signals to and from the non-implanted device during at least some of the instances of the second periods of time.

15. The implantable device of claim 14, further comprising:

a rectifier coupled between the inductor coil and the storage capacitor;

the rectifier configured to convert AC power signals, received from the non-implanted device, to DC signals that are used to charge the storage capacitor of the implantable device during the first periods of time that the inductor coil receives the AC power signals from the non-implanted device;

wherein during the second periods of time the inductor coil of the implantable device does not receive AC power signals from the non-implanted device, and thus, communications signals transmitted between the implantable device and the non-implanted device using the inductor coil of the implantable device are subject to less noise compared to if the communications signals were transmitted at the same times that the inductor coil of the implantable device receives AC power signals from the non-implanted device.

16. The implantable device of claim 12, wherein:

the sensor comprises a passive capacitive pressure sensor whose capacitance changes with changes in pressure and is thereby indicative of pressure; and the active circuitry includes sensor measurement circuitry configured to obtain sensor measurements from the passive capacitive pressure sensor and convert the sensor measurements from analog measurements to digital measurements that are transmitted in one or more communication signals from the implantable device to the non-implanted device.

17. The implantable device of claim 16, further comprising:

one or more reference capacitors;

wherein the sensor measurement circuitry is also configured to obtain reference capacitance measurements of at least one of the one or more reference capacitors and convert the reference capacitance measurements from analog measurements to digital measurements that are stored in memory and/or transmitted in one or more communication signals from the implantable device to the non-implanted device;

wherein changes over time in the reference capacitance measurements are indicative of drift in the active circuitry; and wherein the reference capacitance measurements are used by the implantable device, or the non-implanted device, to compensate for the drift in the active circuitry.

18. The implantable device of claim 16, wherein the implantable device is configured to be implanted in a pulmonary artery, and wherein the sensor measurements obtained using the passive capacitive pressure sensor are indicative of pulmonary artery pressure (PAP).

19. The implantable device of claim 16, wherein:

the active circuitry includes circuitry configured to detect a transition from an instance of the first period of time to an immediately following instance of the second period of time, and in response thereto, trigger use of the sensor measurement circuitry.

20. The implantable device of claim 19, wherein:
during one or more instances of the second periods of time, the operation performed by the active circuitry comprises transmitting one or more communication signals including the device specific information from the implantable device to the non-implanted device.

21. The implantable device of claim 12, wherein the memory of the implantable device comprises non-volatile memory that stores device specific information including:
a patient identifier indicative a patient in which the implantable device is implanted;
sensor linearity calibration data that is used to compensate for a non-linearity of the sensor of the implantable device; and
sensor offset calibration data that is used to compensate for an offset in pressure sensor measurements obtained using the sensor of the implantable device.

* * * * *